US008636678B2

(12) United States Patent
Vess

(10) Patent No.: US 8,636,678 B2
(45) Date of Patent: Jan. 28, 2014

(54) INFLATABLE MEMBER FOR COMPRESSION FOOT CUFF

(75) Inventor: Mark A. Vess, Hanson, MA (US)

(73) Assignee: Covidien LP, Mansfield, MA (US)

( * ) Notice: Subject to any disclaimer, the term of this patent is extended or adjusted under 35 U.S.C. 154(b) by 1589 days.

(21) Appl. No.: 12/166,072

(22) Filed: Jul. 1, 2008

(65) Prior Publication Data

US 2010/0004575 A1    Jan. 7, 2010

(51) Int. Cl.
*A61H 7/00* (2006.01)

(52) U.S. Cl.
USPC ............. 601/148; 601/151; 601/152; 602/13; 602/23

(58) Field of Classification Search
USPC ................... 601/148, 151, 152; 602/13, 23; 128/DIG. 20, DIG. 3
See application file for complete search history.

(56) References Cited

U.S. PATENT DOCUMENTS

| | | |
|---|---|---|
| 2,075,229 A | 3/1937 | Rose |
| 2,199,408 A | 5/1940 | La Liberte |
| 2,533,504 A | 12/1950 | Poor |
| 2,694,395 A | 11/1954 | Brown |
| 2,708,920 A | 5/1955 | Pasturczak |
| 2,880,721 A | 4/1959 | Corcoran |
| D192,777 S | 5/1962 | Pahas |
| 3,164,152 A | 1/1965 | Vere Nicoll |
| 3,245,405 A | 4/1966 | Gardner |
| 3,454,010 A | 7/1969 | Lilligren et al. |
| 3,506,000 A | 4/1970 | Baker |
| 3,521,623 A | 7/1970 | Nichols et al. |
| 3,561,435 A | 2/1971 | Nicholson |
| 3,598,114 A | 8/1971 | Lewis |
| 3,606,880 A | 9/1971 | Ogle, Jr. |
| 3,701,349 A | 10/1972 | Larson |
| 3,728,875 A | 4/1973 | Hartigan et al. |
| 3,760,795 A | 9/1973 | Adelhed |
| 3,786,805 A * | 1/1974 | Tourin ............................ 602/13 |
| 3,824,992 A | 7/1974 | Nicholson et al. |
| 3,826,249 A | 7/1974 | Lee et al. |
| 3,862,629 A | 1/1975 | Rotta |
| 3,866,604 A | 2/1975 | Curless et al. |
| 3,868,952 A | 3/1975 | Hatton |
| 3,877,426 A | 4/1975 | Nirschl |
| 3,888,242 A | 6/1975 | Harris et al. |
| 3,901,221 A | 8/1975 | Nicholson et al. |

(Continued)

FOREIGN PATENT DOCUMENTS

FR    2813770 A1    3/2002

OTHER PUBLICATIONS

Merriam-Webster Dictionary; Definition of "size"; www.merriam-webster.com; accessed Sep. 22, 2012.*

(Continued)

*Primary Examiner* — Patricia Bianco
*Assistant Examiner* — Caitlin Carreiro
(74) *Attorney, Agent, or Firm* — John Paul Mello, Esq.

(57) ABSTRACT

A foot cuff that is inflatable to apply compression to the foot to promote blood flow has a bladder formed of two layers of material secured together. An outer layer includes a foot-underlying portion that has a greater thickness and rigidity that an opposing inner layer. The outer layer directs expansion of the bladder upon inflation in the direction of the inner layer and toward the foot for increasing compressive force applied to the foot.

12 Claims, 10 Drawing Sheets

(56) References Cited

U.S. PATENT DOCUMENTS

| | | |
|---|---|---|
| 3,901,225 A | 8/1975 | Sconce |
| 3,920,006 A | 11/1975 | Lapidus |
| 4,013,069 A | 3/1977 | Hasty |
| 4,029,087 A | 6/1977 | Dye et al. |
| 4,030,488 A | 6/1977 | Hasty |
| 4,066,084 A | 1/1978 | Tillander |
| 4,091,804 A | 5/1978 | Hasty |
| 4,133,311 A | 1/1979 | Karczewski |
| 4,153,050 A | 5/1979 | Bishop et al. |
| 4,156,425 A * | 5/1979 | Arkans ................ 601/152 |
| 4,168,063 A | 9/1979 | Rowland |
| 4,198,961 A | 4/1980 | Arkans |
| 4,202,312 A | 5/1980 | Mori et al. |
| 4,202,325 A | 5/1980 | Villari et al. |
| 4,206,751 A | 6/1980 | Schneider |
| 4,207,875 A | 6/1980 | Arkans |
| 4,207,876 A | 6/1980 | Annis |
| 4,253,449 A | 3/1981 | Arkans et al. |
| 4,270,527 A | 6/1981 | Peters et al. |
| 4,280,485 A | 7/1981 | Arkans |
| 4,311,135 A | 1/1982 | Brueckner et al. |
| 4,320,746 A | 3/1982 | Arkans et al. |
| 4,338,686 A | 7/1982 | Bell |
| 4,372,297 A | 2/1983 | Perlin |
| 4,375,217 A | 3/1983 | Arkans |
| 4,408,599 A | 10/1983 | Mummert |
| 4,409,976 A | 10/1983 | Pence |
| 4,417,587 A | 11/1983 | Ichinomiya et al. |
| 4,419,988 A | 12/1983 | Mummert |
| 4,442,834 A * | 4/1984 | Tucker et al. ............. 602/13 |
| 4,453,538 A | 6/1984 | Whitney |
| 4,531,516 A | 7/1985 | Poole et al. |
| 4,580,816 A | 4/1986 | Campbell et al. |
| 4,597,384 A | 7/1986 | Whitney |
| 4,597,385 A | 7/1986 | Watson |
| 4,614,179 A | 9/1986 | Gardner et al. |
| 4,614,180 A | 9/1986 | Gardner et al. |
| 4,632,103 A | 12/1986 | Fabricant et al. |
| 4,696,289 A | 9/1987 | Gardner et al. |
| 4,702,232 A | 10/1987 | Gardner et al. |
| 4,702,234 A | 10/1987 | Huntjens |
| 4,721,101 A * | 1/1988 | Gardner et al. ........... 601/152 |
| 4,722,332 A | 2/1988 | Saggers |
| 4,730,606 A | 3/1988 | Leininger |
| 4,730,610 A | 3/1988 | Graebe |
| 4,762,121 A | 8/1988 | Shienfeld |
| 4,805,601 A | 2/1989 | Eischen, Sr. |
| 4,827,912 A * | 5/1989 | Carrington et al. ........ 601/152 |
| RE32,939 E | 6/1989 | Gardner et al. |
| RE32,940 E | 6/1989 | Gardner et al. |
| 4,841,956 A | 6/1989 | Gardner et al. |
| D302,301 S | 7/1989 | Robinette-Lehman |
| 4,844,058 A | 7/1989 | Vogelbach |
| 4,883,073 A | 11/1989 | Aziz |
| 4,920,971 A | 5/1990 | Blessinger |
| 4,938,208 A | 7/1990 | Dye |
| 4,945,905 A | 8/1990 | Dye et al. |
| 4,977,891 A | 12/1990 | Grim |
| 4,979,953 A | 12/1990 | Spence |
| 4,993,409 A | 2/1991 | Grim |
| 5,000,164 A | 3/1991 | Cooper |
| 5,007,411 A | 4/1991 | Dye |
| 5,014,681 A | 5/1991 | Neeman et al. |
| 5,022,387 A | 6/1991 | Hasty |
| 5,062,414 A | 11/1991 | Grim |
| 5,069,219 A | 12/1991 | Knoblich |
| 5,078,128 A | 1/1992 | Grim et al. |
| 5,094,252 A | 3/1992 | Stumpf |
| 5,113,877 A | 5/1992 | Johnson, Jr. et al. |
| 5,193,549 A | 3/1993 | Bellin et al. |
| 5,218,954 A | 6/1993 | van Bemmelen |
| 5,235,703 A | 8/1993 | Maynard |
| D341,424 S | 11/1993 | Lurie |
| 5,277,697 A | 1/1994 | France et al. |
| 5,288,286 A | 2/1994 | Davis et al. |
| 5,310,400 A | 5/1994 | Rogers et al. |
| 5,334,135 A | 8/1994 | Grim et al. |
| 5,354,260 A | 10/1994 | Cook |
| 5,372,575 A | 12/1994 | Sebastian |
| RE34,883 E | 3/1995 | Grim |
| 5,396,896 A | 3/1995 | Tumey et al. |
| 5,399,152 A | 3/1995 | Habermeyer et al. |
| 5,400,529 A | 3/1995 | Bell et al. |
| 5,407,418 A | 4/1995 | Szpur |
| 5,407,421 A | 4/1995 | Goldsmith |
| D358,216 S | 5/1995 | Dye |
| 5,413,582 A | 5/1995 | Eaton |
| 5,415,624 A | 5/1995 | Williams |
| 5,425,742 A | 6/1995 | Joy |
| 5,437,610 A | 8/1995 | Cariapa et al. |
| 5,450,858 A | 9/1995 | Zablotsky et al. |
| 5,453,082 A | 9/1995 | Lamont |
| 5,458,562 A | 10/1995 | Cooper |
| 5,464,385 A | 11/1995 | Grim |
| 5,484,392 A | 1/1996 | Sydor et al. |
| D376,013 S | 11/1996 | Sandman et al. |
| 5,575,762 A | 11/1996 | Peeler et al. |
| 5,577,998 A | 11/1996 | Johnson, Jr. et al. |
| 5,584,798 A | 12/1996 | Fox |
| 5,588,955 A | 12/1996 | Johnson, Jr. et al. |
| 5,591,200 A | 1/1997 | Cone et al. |
| 5,626,556 A | 5/1997 | Tobler et al. |
| 5,634,889 A | 6/1997 | Gardner et al. |
| 5,649,954 A | 7/1997 | McEwen |
| 5,653,244 A | 8/1997 | Shaw |
| 5,660,182 A | 8/1997 | Kuroshaki et al. |
| 5,669,390 A | 9/1997 | McCormick et al. |
| 5,669,872 A | 9/1997 | Fox |
| 5,674,262 A | 10/1997 | Tumey |
| 5,678,558 A | 10/1997 | Johnson |
| 5,688,225 A | 11/1997 | Walker |
| 5,690,672 A | 11/1997 | Cohen |
| 5,711,757 A | 1/1998 | Bryant |
| 5,733,249 A | 3/1998 | Katzin et al. |
| 5,746,213 A | 5/1998 | Marks |
| 5,769,801 A | 6/1998 | Tumey et al. |
| 5,795,312 A | 8/1998 | Dye |
| 5,797,851 A | 8/1998 | Byrd |
| D397,797 S | 9/1998 | Chiang |
| 5,806,208 A | 9/1998 | French |
| 5,823,981 A | 10/1998 | Grim et al. |
| 5,830,164 A | 11/1998 | Cone et al. |
| 5,833,639 A | 11/1998 | Nunes et al. |
| 5,840,049 A | 11/1998 | Tumey et al. |
| 5,843,007 A | 12/1998 | McEwen et al. |
| D405,180 S | 2/1999 | Reina |
| 5,864,880 A | 2/1999 | Adam |
| 5,868,690 A | 2/1999 | Eischen, Sr. |
| 5,876,359 A | 3/1999 | Bock et al. |
| 5,891,065 A | 4/1999 | Cariapa et al. |
| D411,301 S | 6/1999 | Hampson et al. |
| 5,931,797 A | 8/1999 | Tumey et al. |
| 5,951,502 A | 9/1999 | Peeler et al. |
| 5,954,676 A | 9/1999 | Kramer, III |
| 5,971,947 A | 10/1999 | McNally et al. |
| 5,987,779 A | 11/1999 | Litchfield et al. |
| 5,988,704 A | 11/1999 | Ryhman |
| 5,989,204 A | 11/1999 | Lina |
| 5,991,654 A | 11/1999 | Tumey et al. |
| 5,997,495 A | 12/1999 | Cook et al. |
| 6,001,122 A | 12/1999 | Lyles |
| 6,010,471 A | 1/2000 | Ben-Noon |
| 6,014,823 A | 1/2000 | Lakic |
| 6,024,714 A | 2/2000 | Katzin |
| 6,036,718 A | 3/2000 | Ledford et al. |
| 6,066,107 A | 5/2000 | Habermeyer |
| 6,083,185 A | 7/2000 | Lamont |
| 6,228,044 B1 | 5/2001 | Jensen et al. |
| 6,245,023 B1 | 6/2001 | Clemmons |
| 6,273,866 B2 | 8/2001 | Thomas et al. |
| 6,290,662 B1 | 9/2001 | Morris et al. |
| 6,293,918 B1 | 9/2001 | Wang |
| 6,306,112 B2 | 10/2001 | Bird |
| 6,315,745 B1 * | 11/2001 | Kloecker ................ 602/13 |

(56) References Cited

U.S. PATENT DOCUMENTS

| | | |
|---|---|---|
| 6,319,215 B1 | 11/2001 | Manor et al. |
| 6,361,496 B1 | 3/2002 | Zikorus et al. |
| 6,361,548 B1 | 3/2002 | McEwen |
| 6,406,450 B1 | 6/2002 | Kowalczyk et al. |
| 6,416,534 B1 | 7/2002 | Montagnino et al. |
| 6,423,017 B2 | 7/2002 | Brotz |
| 6,436,064 B1 | 8/2002 | Kloecker |
| 6,440,093 B1 | 8/2002 | McEwen et al. |
| 6,447,460 B1 | 9/2002 | Zheng et al. |
| 6,447,467 B1 | 9/2002 | Barak |
| 6,460,197 B2 | 10/2002 | Huang |
| 6,463,934 B1 | 10/2002 | Johnson, Jr. et al. |
| 6,468,237 B1 | 10/2002 | Lina |
| 6,478,745 B2 | 11/2002 | Nakagawa et al. |
| 6,478,757 B1 | 11/2002 | Barak |
| 6,488,643 B1 | 12/2002 | Tumey et al. |
| 6,493,568 B1 | 12/2002 | Bell et al. |
| 6,494,852 B1 | 12/2002 | Barak et al. |
| 6,506,206 B1 | 1/2003 | Guzman et al. |
| 6,525,238 B2 | 2/2003 | Corrales |
| 6,528,697 B1 | 3/2003 | Knutson et al. |
| 6,537,298 B2 | 3/2003 | Dedo |
| 6,544,202 B2 | 4/2003 | McEwen et al. |
| 6,551,249 B2 | 4/2003 | Ashida et al. |
| 6,551,264 B1 | 4/2003 | Cawley et al. |
| 6,557,704 B1 | 5/2003 | Randolph |
| 6,582,383 B2 | 6/2003 | Horning |
| 6,585,669 B2 | 7/2003 | Manor et al. |
| 6,589,194 B1 | 7/2003 | Calderon et al. |
| 6,589,534 B1 | 7/2003 | Shaul et al. |
| 6,592,534 B1 | 7/2003 | Rutt et al. |
| 6,629,941 B1 | 10/2003 | Ishibashi et al. |
| 6,632,188 B2 | 10/2003 | Thomas et al. |
| D482,792 S | 11/2003 | McCormick et al. |
| 6,672,311 B2 | 1/2004 | Rindfleish |
| 6,681,772 B2 | 1/2004 | Atwater et al. |
| 6,682,497 B2 | 1/2004 | Jensen et al. |
| 6,682,547 B2 | 1/2004 | McEwen et al. |
| 6,746,470 B2 | 6/2004 | McEwen et al. |
| 6,762,337 B2 | 7/2004 | Boukanov et al. |
| 6,766,599 B2 | 7/2004 | Baek |
| 6,785,985 B2 | 9/2004 | Marvin et al. |
| 6,846,295 B1 | 1/2005 | Ben-Nun |
| 6,869,409 B2 | 3/2005 | Rothman et al. |
| 6,893,409 B1 | 5/2005 | Lina |
| 6,916,298 B2 | 7/2005 | VanBrunt et al. |
| 6,918,393 B2 | 7/2005 | Rugfelt et al. |
| 6,921,373 B1 | 7/2005 | Bernstein |
| 6,945,944 B2 | 9/2005 | Kuiper et al. |
| D513,324 S | 12/2005 | Cook et al. |
| 6,988,329 B2 | 1/2006 | Marvin et al. |
| 6,988,992 B2 | 1/2006 | Just et al. |
| D517,695 S * | 3/2006 | Gillis et al. .................. D24/169 |
| 7,008,390 B2 | 3/2006 | Miotto et al. |
| 7,010,823 B2 | 3/2006 | Baek |
| 7,047,670 B2 | 5/2006 | Marvin et al. |
| 7,063,676 B2 | 6/2006 | Barak et al. |
| 7,070,567 B2 | 7/2006 | Mizukoshi et al. |
| 7,104,967 B2 | 9/2006 | Rothman et al. |
| 7,135,007 B2 | 11/2006 | Scott et al. |
| 7,150,720 B2 | 12/2006 | Adkins et al. |
| 7,153,270 B2 | 12/2006 | Sano et al. |
| 7,166,077 B2 | 1/2007 | Millay et al. |
| 7,276,037 B2 | 10/2007 | Ravikumar |
| 7,282,038 B2 | 10/2007 | Gillis et al. |
| 7,354,410 B2 | 4/2008 | Perry et al. |
| D569,985 S | 5/2008 | Ganapathy et al. |
| 7,374,550 B2 | 5/2008 | Hansen et al. |
| 7,384,584 B2 | 6/2008 | Jerome et al. |
| 2001/0018564 A1 | 8/2001 | Manor et al. |
| 2002/0022791 A1 | 2/2002 | Morris et al. |
| 2002/0069731 A1 | 6/2002 | Soucy |
| 2002/0099297 A1 | 7/2002 | Nakagawa et al. |
| 2002/0188315 A1 | 12/2002 | Guzman et al. |
| 2003/0125649 A1 | 7/2003 | McIntosh et al. |
| 2003/0187378 A1 | 10/2003 | Gaylord et al. |
| 2004/0039317 A1 | 2/2004 | Souney et al. |
| 2004/0064077 A1 | 4/2004 | Dillon |
| 2004/0068290 A1 * | 4/2004 | Bates et al. .................. 606/202 |
| 2004/0171971 A1 | 9/2004 | Ravikumar et al. |
| 2004/0181156 A1 | 9/2004 | Kingsford et al. |
| 2004/0236258 A1 | 11/2004 | Burns et al. |
| 2005/0027218 A1 | 2/2005 | Filtvedt et al. |
| 2005/0055913 A1 | 3/2005 | Nugue et al. |
| 2005/0121041 A1 | 6/2005 | Barnitz |
| 2005/0143682 A1 | 6/2005 | Cook et al. |
| 2005/0145256 A1 | 7/2005 | Howard et al. |
| 2005/0171461 A1 | 8/2005 | Pick |
| 2005/0187501 A1 | 8/2005 | Ravikumar |
| 2005/0203452 A1 | 9/2005 | Weston et al. |
| 2005/0211580 A1 | 9/2005 | Kaszubski et al. |
| 2005/0215935 A1 | 9/2005 | Ritter |
| 2005/0261615 A1 | 11/2005 | Weston |
| 2006/0004310 A1 | 1/2006 | Parizot |
| 2006/0004311 A1 | 1/2006 | Hargrave et al. |
| 2006/0135894 A1 | 6/2006 | Linnane et al. |
| 2006/0161081 A1 | 7/2006 | Barak et al. |
| 2006/0178606 A1 | 8/2006 | Logue et al. |
| 2006/0189905 A1 | 8/2006 | Eischen, Sr. |
| 2006/0189907 A1 | 8/2006 | Pick et al. |
| 2007/0010765 A1 | 1/2007 | Rothman et al. |
| 2007/0010770 A1 | 1/2007 | Gildersleeve |
| 2007/0049852 A1 | 3/2007 | Linnane et al. |
| 2007/0129658 A1 | 6/2007 | Hampson et al. |
| 2007/0135742 A1 * | 6/2007 | Meyer et al. .................. 601/152 |
| 2007/0135743 A1 * | 6/2007 | Meyer .......................... 601/152 |
| 2007/0135836 A1 | 6/2007 | McEwen et al. |
| 2007/0161933 A1 | 7/2007 | Ravikumar |
| 2007/0282233 A1 * | 12/2007 | Meyer et al. .................. 602/23 |

OTHER PUBLICATIONS

European Search Report for EP10174333.4 dated Oct. 18, 2010, 6 pages.
Tyco Healthcare Kendall, Prevention Gets Personal brochure, Mar. 2001, pp. 1, 2, and 4.
Tyco Healthcare Kendall, SCD Response Sequential Compression System brochure, Mar. 2000, pp. 1-2.
Tyco Healthcare Kendall, SCD Soft Sleeve brochure, Apr. 2001, pp. 1-2.
The Kendall Company, Vascular Therapy Products catalog, Jan. 1996, pp. 8-5 through 8-7.
European Search Report for EP 09 16 4111 dated Aug. 4, 2009, 7 pgs.

* cited by examiner

INFLATABLE MEMBER FOR COMPRESSION FOOT CUFF

FIELD OF THE INVENTION

The present invention generally relates to an inflatable member for a compression foot cuff.

BACKGROUND

Compression devices for applying compressive forces to a selected area of a wearer's anatomy are generally employed to improve blood flow in the selected area. Compression devices that provide intermittent pulses of a compressed fluid (i.e., air) to inflate at least one inflatable chamber in a cuff or sleeve are particularly useful. This cyclic application of pressure provides a non-invasive prophylaxis to reduce the incidence of deep vein thrombosis (DVT), and the like. These compression devices find particular use during surgery or long periods of immobility on patients with high-risk conditions such as obesity, advanced age, malignancy, or prior thromboembolism. Patients who develop this condition often have swelling (edema) and tissue breakdown (venous stasis ulcer) in the lower leg. When a DVT occurs, the valves that are located within the veins of the leg can be damaged, which in turn can cause stasis and high pressure in the veins of the lower leg.

Generally, these compression devices are fluidly coupled to a source of pressurized fluid by one or more air tubes. Additionally, each compression device includes a flexible shell having one or more bladders disposed therein. The compression device is placed around the patient's foot or other selected portion whereupon a pressurized fluid is delivered into the bladder creating pressure at the part or parts of the body in contact with the bladder.

Compression cuffs adapted for use with a patient's foot may be used by themselves or combined with one or more additional compression cuffs or sleeves that are disposed on portions of a patient's leg for improving the treatment regimen. In general, each of the additional compression sleeves includes a plurality of separate inflatable chambers that are progressively arranged along a longitudinal axis of the sleeve from a lower portion to an upper portion of the limb. A pressure source, e.g. a controller, is provided for intermittently forming a pressure pulse within these inflatable chambers from a source of pressurized fluid during periodic compression cycles. The compression sleeves provide a pressure gradient along the patient's limbs during these compression cycles which progressively decreases from the lower portion to the upper portion of the limb (e.g. from the ankle to the thigh).

Compression cuffs that are adapted for use with a patient's foot generally include a heel strap with a tab portion that is adapted to fit around a portion of the patient's heel. This arrangement allows the compression cuff to be wrapped around and releasably attached to the patient's foot. The compression cuff may include a generally rigid sole to direct expansion of the inflatable chamber toward the wearer's foot. The rigid sole needs to be located under that portion of the inflatable member that is acting on the portion of the foot to produce blood flow out of the foot. Conventionally, the rigid sole is temporarily attached to the bladder by double stick tape. Final location and positioning of the rigid sole may be carried out by stitching. For example, the bladder is typically stitched to an outer wrap of the foot cuff. The stitching can be arranged so that it captures the rigid sole in position relative to the bladder, as well as the outer wrap. This requires care and precision in manufacturing the foot cuff.

SUMMARY

In one aspect of the present invention, an inflatable bladder for use in a compression foot cuff configured to be secured to a foot of a wearer generally comprises a fluid-impermeable inner bladder layer for being positioned adjacent to a foot of a wearer. A fluid-impermeable, integrally formed outer bladder layer is secured in opposing relation to the inner bladder layer to define an inflatable chamber. The inner and outer bladder layers define a foot-underlying portion of the bladder that is sized and shaped to underlie the wearer's foot and a wing portion extending laterally outwardly from the foot-underlying portion. A thickness of the outer bladder layer at the foot-underlying portion is greater than a thickness of the inner bladder layer to provide rigidity to the outer bladder layer so that the inflatable chamber expands more toward the wearer's foot than away from wearer's foot when the foot cuff is secured to the wearer's foot, and a thickness of the outer layer at the foot-underlying portion is greater than a thickness of the outer layer at the wing portion so that the wing portion of the bladder is more flexible than the foot-underlying portion of the outer layer to wrap around a superior portion of the wearer's foot.

Another aspect of the present invention is a method of making a compression foot cuff configured to be secured to a foot of a wearer, the compression foot cuff having a foot-underlying portion for underlying the wearer's foot. A fluid-impermeable inner bladder layer having a first thickness is provided. An integral outer bladder layer including a foot-underlying portion and a wing portion extending laterally outward from the foot-underlying portion of the cuff is molded as one piece. The foot-underlying portion has a second thickness that is greater than the first thickness of the inner layer, and the wing portion has a third thickness that is less than the second thickness. The inner bladder layer and the outer bladder layer are welded to one another along a line to define an inflatable chamber at the foot-underlying portion of the cuff.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1A:
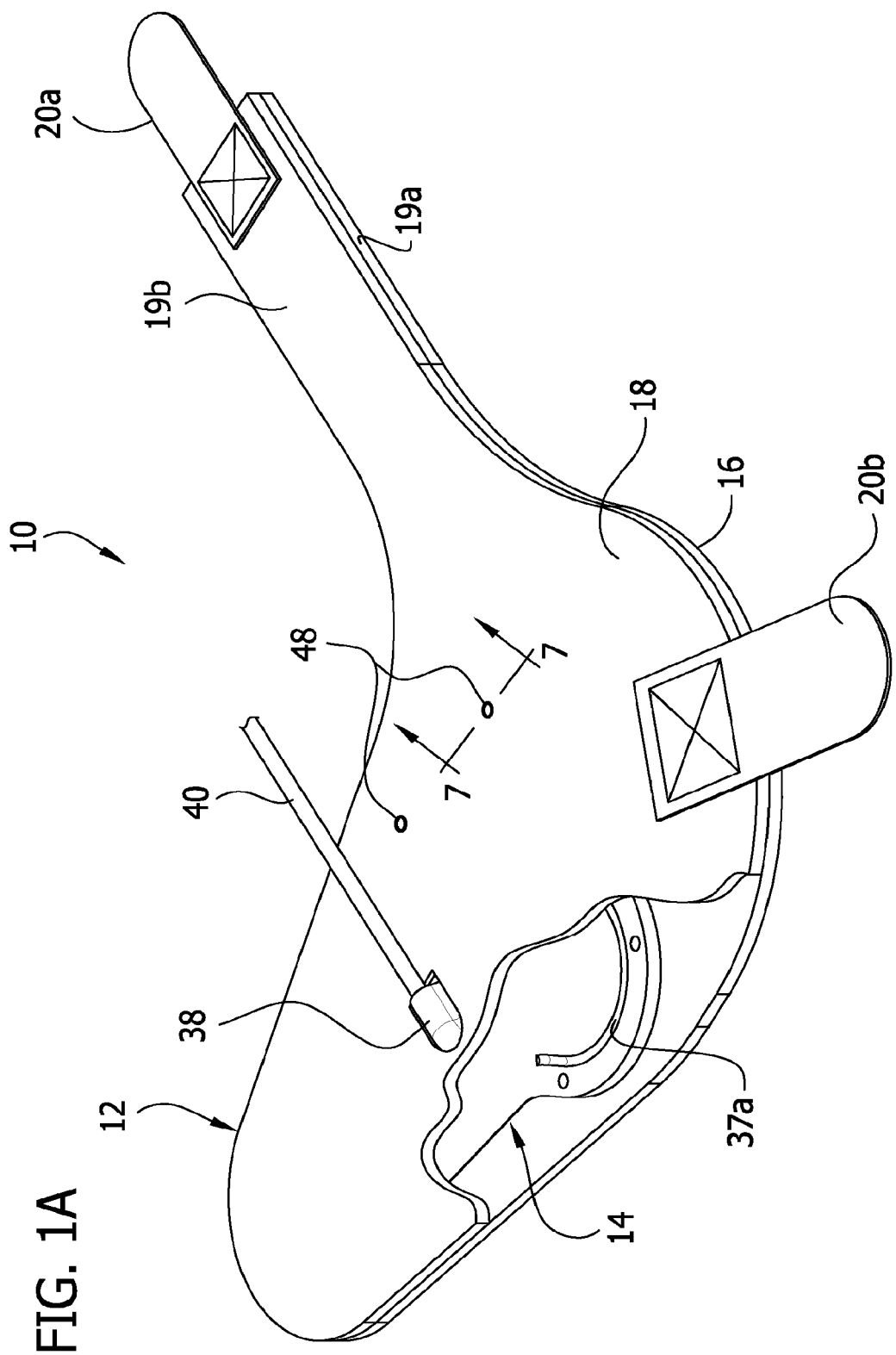
FIG. 1A is a bottom side perspective of a first embodiment of a compression foot cuff in accordance with the present disclosure with portions of the cuff broken away to show internal structure.

Referring now to the drawings, a compression foot cuff for applying compressive pressure to a wearer's foot is generally indicated at 10. The foot cuff is adapted for use in a compression therapy system, which further includes a supply of pressurized air (not shown) and tubing 40 connecting the supply of pressurized air to the foot cuff.

Figure 1B:
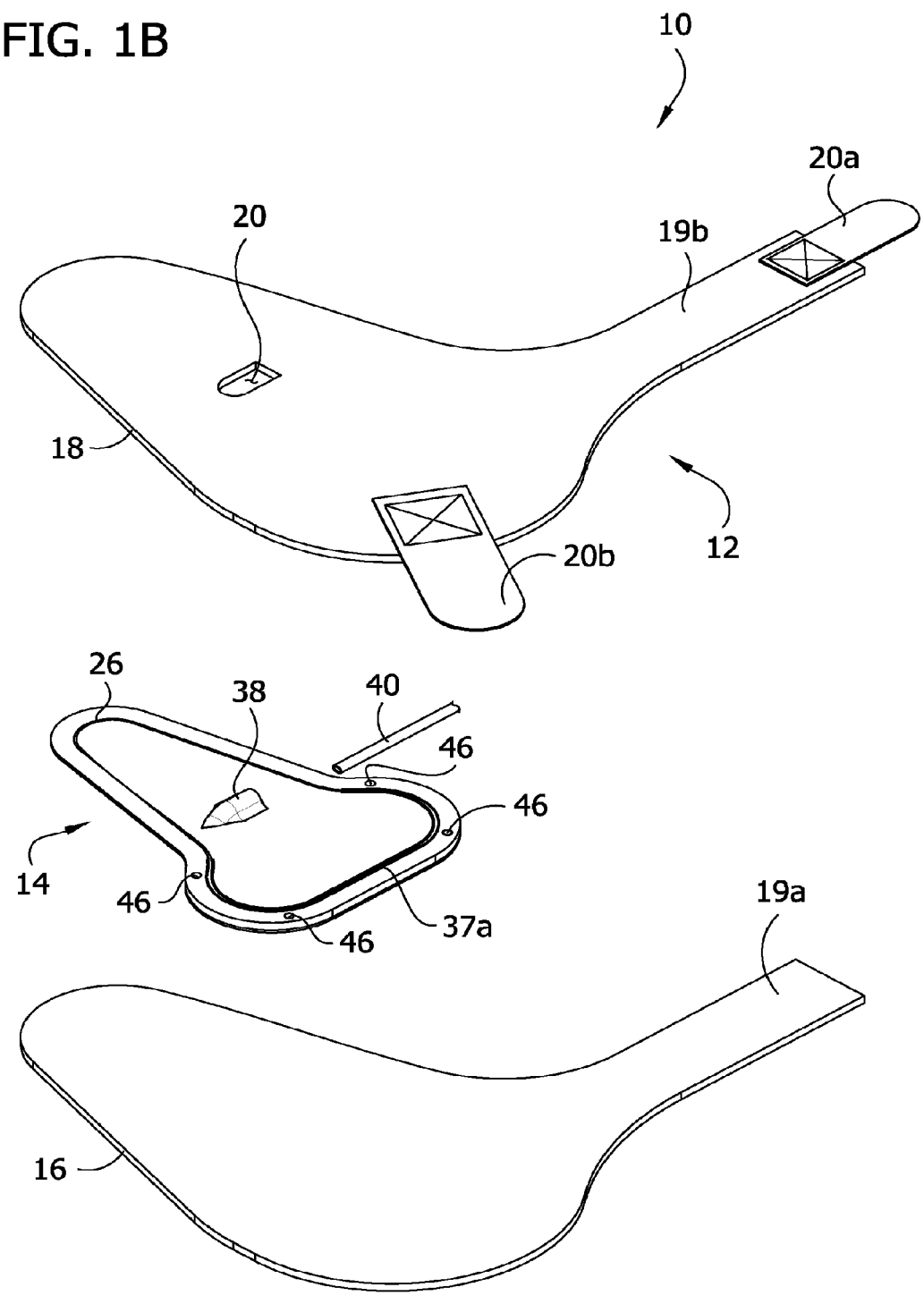
FIG. 1B is an exploded perspective of the compression foot cuff.
Figure 2:
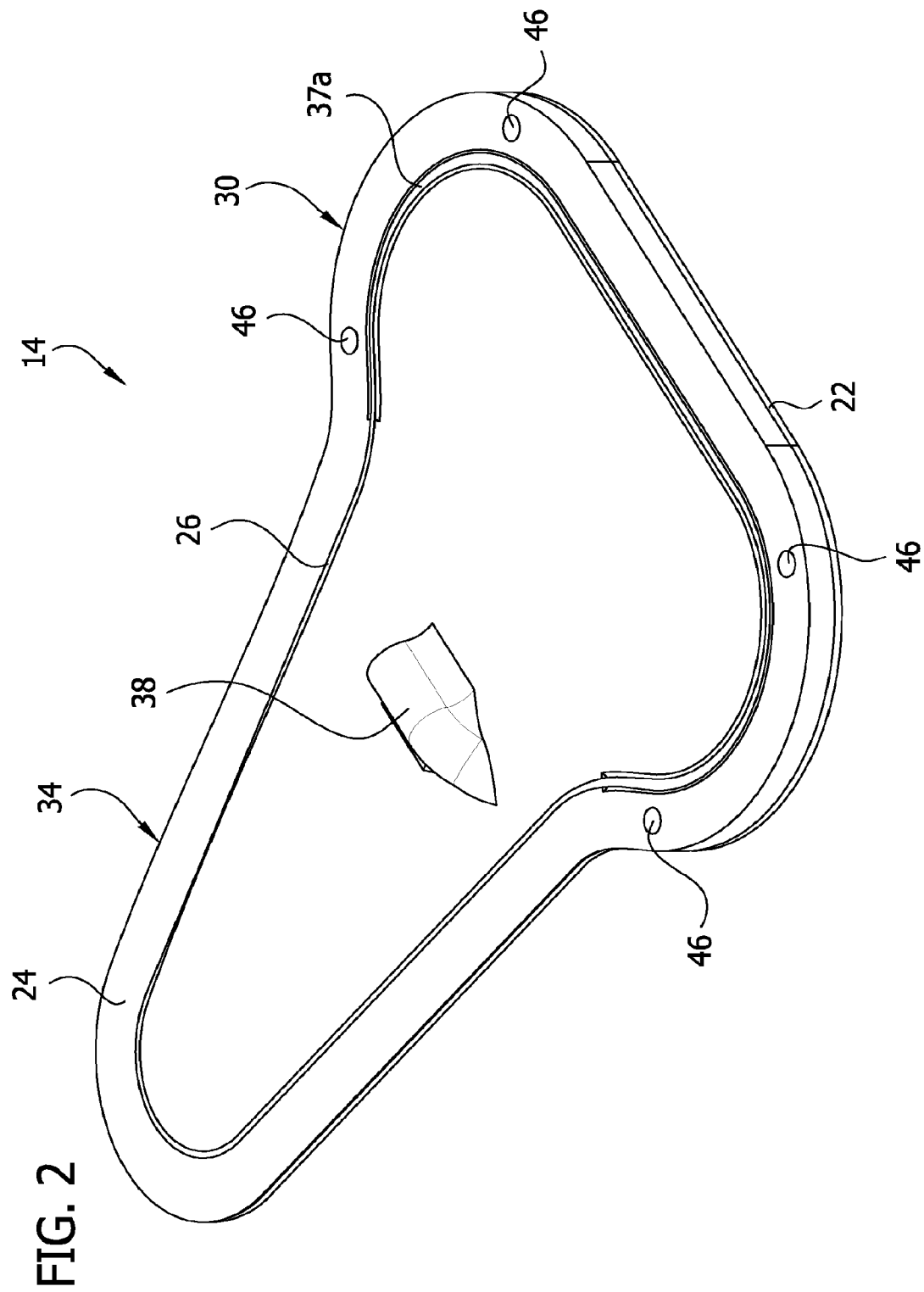
FIG. 2 is a bottom side perspective of an inflatable member of the foot cuff removed from the foot cuff.
Figure 3:
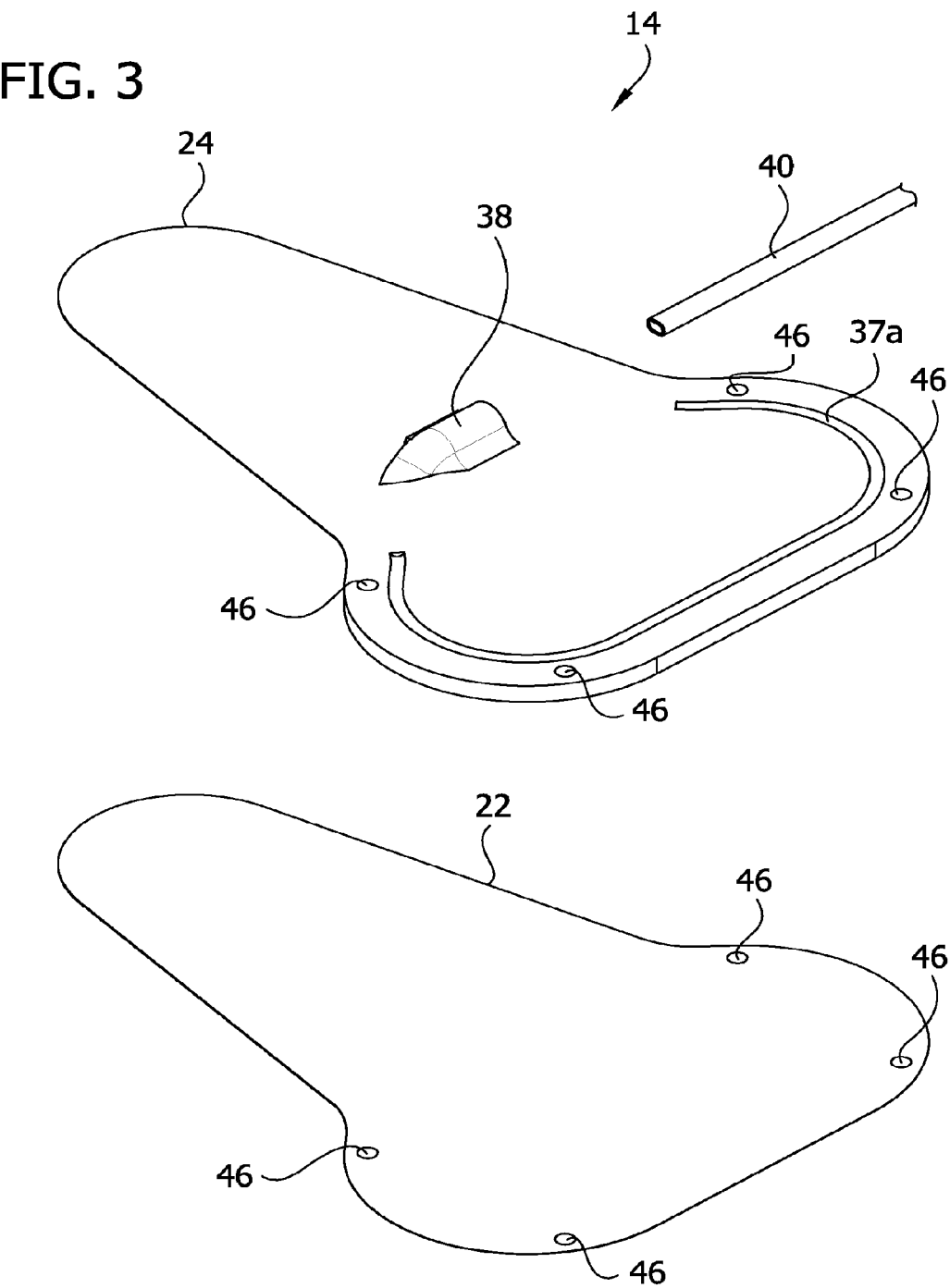
FIG. 3 is an exploded perspective of the inflatable member.
Figure 4:
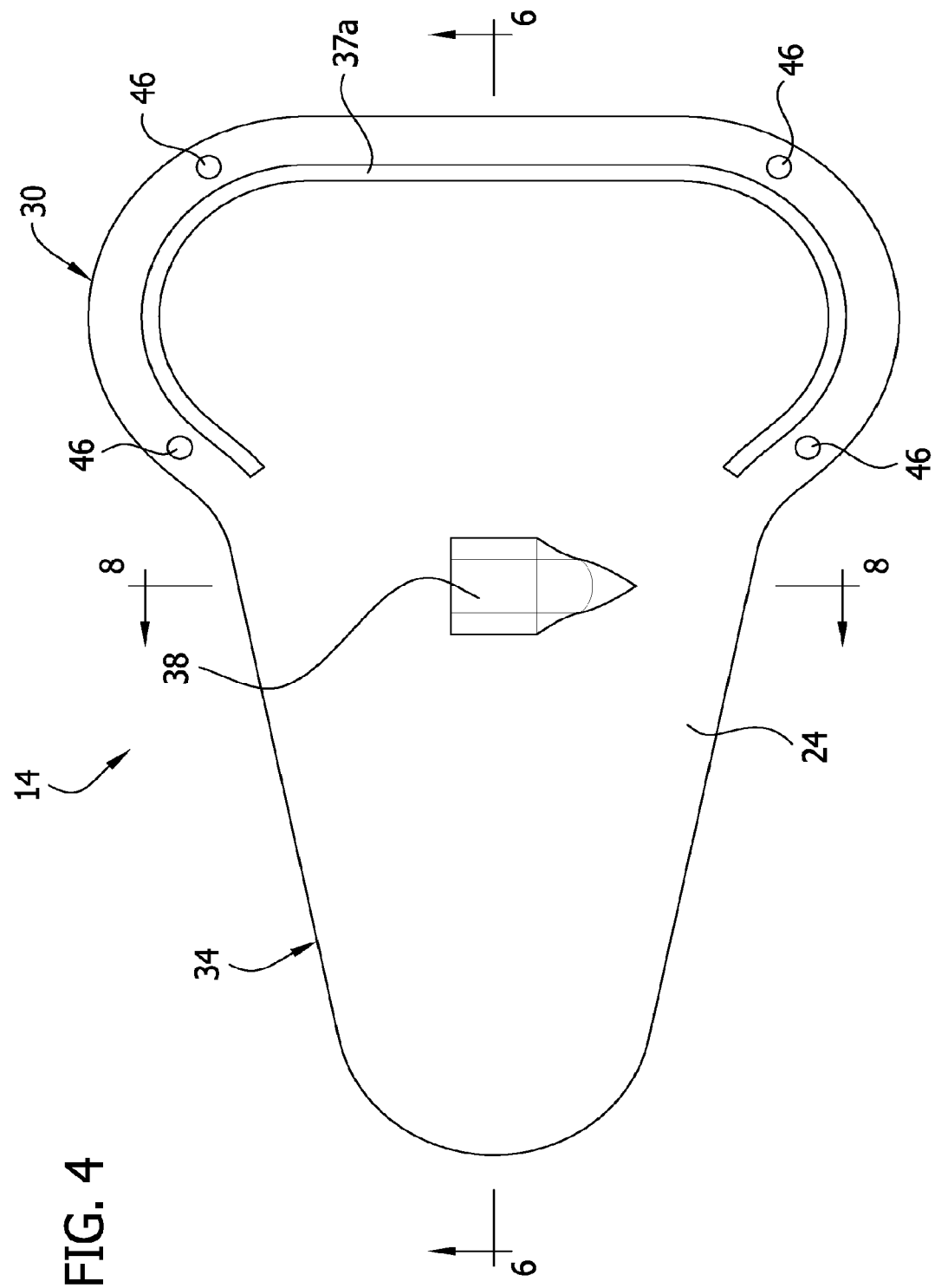
FIG. 4 is a bottom plan view of the inflatable member.
Figure 5:
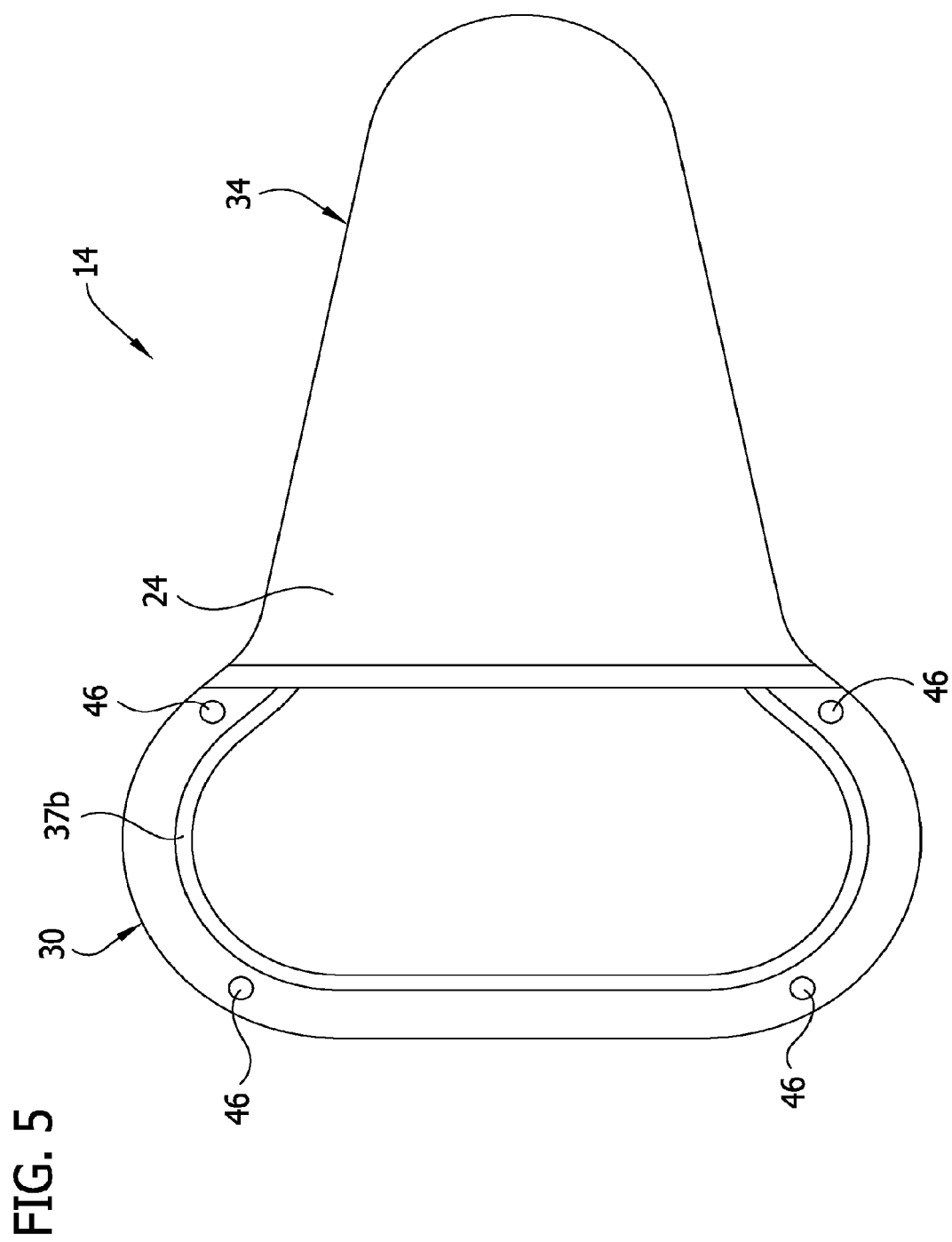
FIG. 5 is a top plan view of an outer layer of the inflatable member.

As shown best in FIGS. 1A and 1B, the foot cuff 10 includes an envelope, generally indicated at 12, substantially enveloping or enclosing a bladder (broadly, an inflatable member), generally indicated at 14. The envelope 12 includes an inner liner 16 and an outer cover 18 secured to one another generally adjacent to corresponding perimeters of the layers to define an interior space for receiving and substantially enclosing the bladder 14 therein. The inner liner 16 and the outer cover 18 may be fixedly secured to one another at their peripheral edge margins, such as by heat welding, adhesives, sewing or other suitable ways. Alternatively, the inner liner 16 and the outer cover 18 may be releasably secured to one another by suitable releasable fasteners (not shown) known to those having ordinary skill in the art. In use the inner liner 16 is adjacent to the wearer's foot and the outer cover 18 is located farthest from the foot. As used herein, the terms "inner" and "outer" indicate relative positions of respective components and surfaces with respect to the skin of the wearer's body part when the compression device is secured to the body part, and as such, an "inner" component or surface is more adjacent to the skin of the body part than an "outer" component or surface.

Inner liner 16 and outer cover 18 of the envelope 12 include ankle strap portions 19a and 19b respectively. Ankle strap portions 19a, 19b have a longitudinally projecting configuration for wrapping about a portion of the back of the foot adjacent to the ankle. The ankle strap portions 19a, 19b can be sewn, RF welded, or sonic welded. However, in the illustrated embodiments, the ankle strap portions 19a, 19b are formed as one piece with the inner liner 16 and outer cover 18, respectively. Respective fastening tabs 20a, 20b are secured to the strap portion 19b and a main portion of the cuff. The fastening tabs 20a, 20b comprise releasable fastener components such as one of a hook component and a loop component for securing the cuff 10 in a wrapped configuration around a foot of a user. Other ways of releasably securing the cuff 10 around the foot of a user are within the scope of the present invention.

The inner liner 16 of the envelope 12 is adapted for contacting the foot. The inner liner 16 is in one embodiment fabricated from a chemically treated material, with wicking ability, for wicking away moisture from the skin. In one embodiment, the inner liner 16 includes a mesh-like fabric capable of wicking moisture away from the patient's skin. Furthermore, the inner liner 16 can be faced with a soft material toward the treatment surface of the patient. For example, the material can be a thin layer of open celled porous foam, napped cloth, or a layer of vapor permeable cloth. The inner liner 16 may be formed from other materials. It is to be understood that the cuff 10 may not include an inner liner within the scope of the present invention.

The outer cover 18 is configured for providing the attachment surface for hook and loop fastening tabs 20a, 20b of cuff 10. For example, the outer cover 18 may comprise a loop-type fastening component and the tabs 20a, 20b may be hook fastening components. Moreover, the outer layer 18 provides a soft material for cushioning effect against the top portion of the feet and may be fabricated from similar materials as the inner liner 16 and in similar dimensions therewith for corresponding geometry. Alternatively, outer cover 18 may be fabricated from a laminated material, such as, for example, Sontara® fabric, open cell urethane foam, or loop fabric. The inner liner 16 may be formed from other materials. It is to be understood that the cuff 10 may not include an outer cover within the scope of the present invention.

Figure 6:
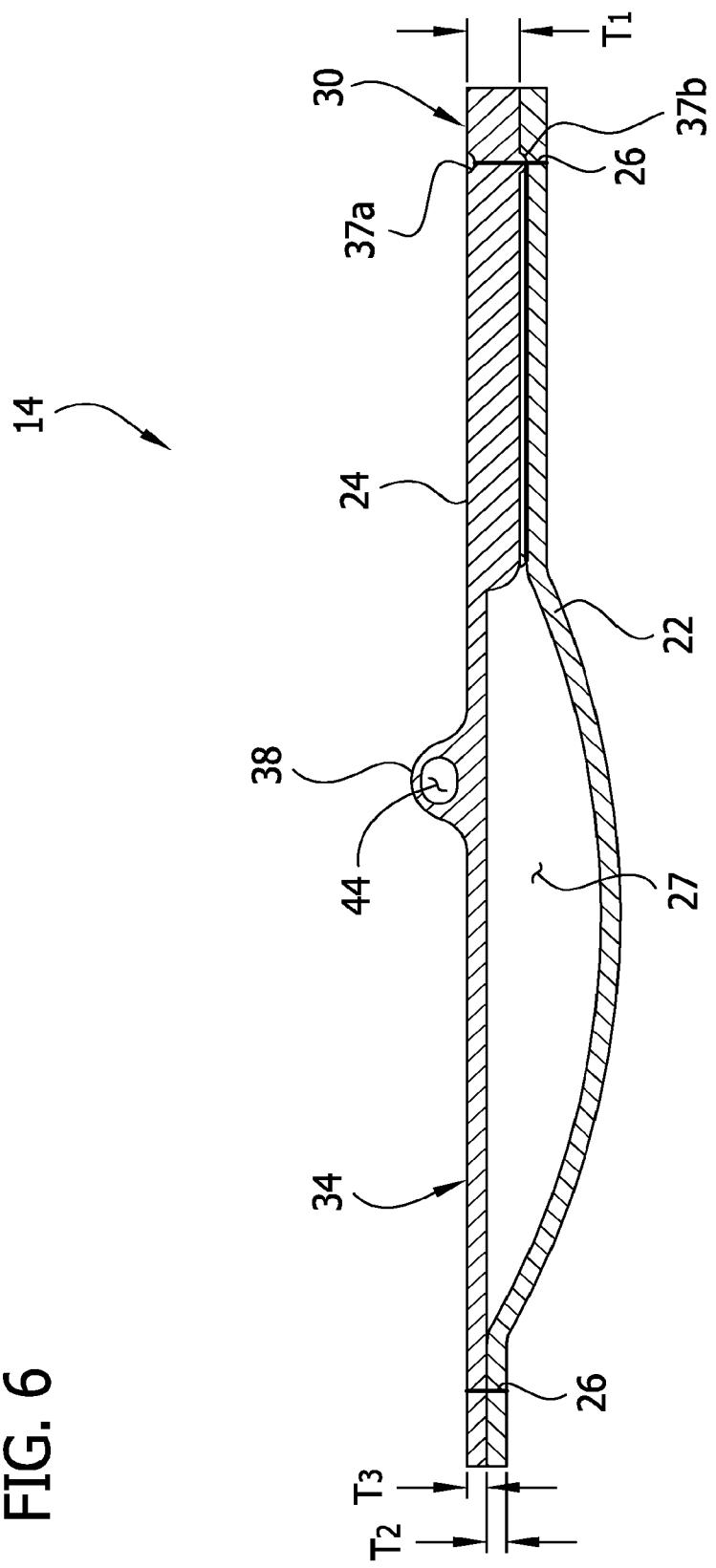
FIG. 6 is a section taken along the line 6-6 in FIG. 4.
Figure 7:
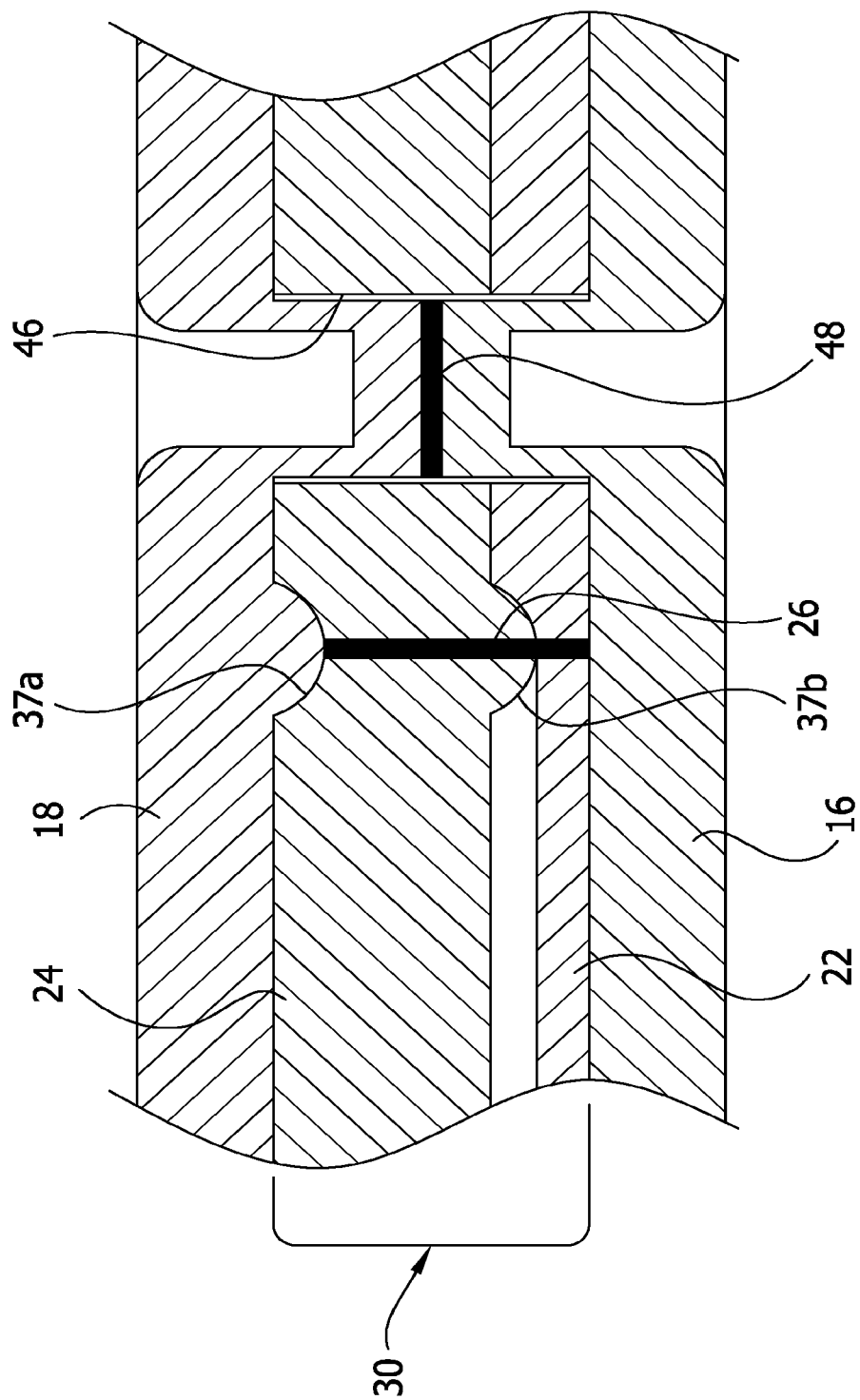
FIG. 7 is a fragmentary section taken along line 7-7 in FIG. 1A.
Figure 8:
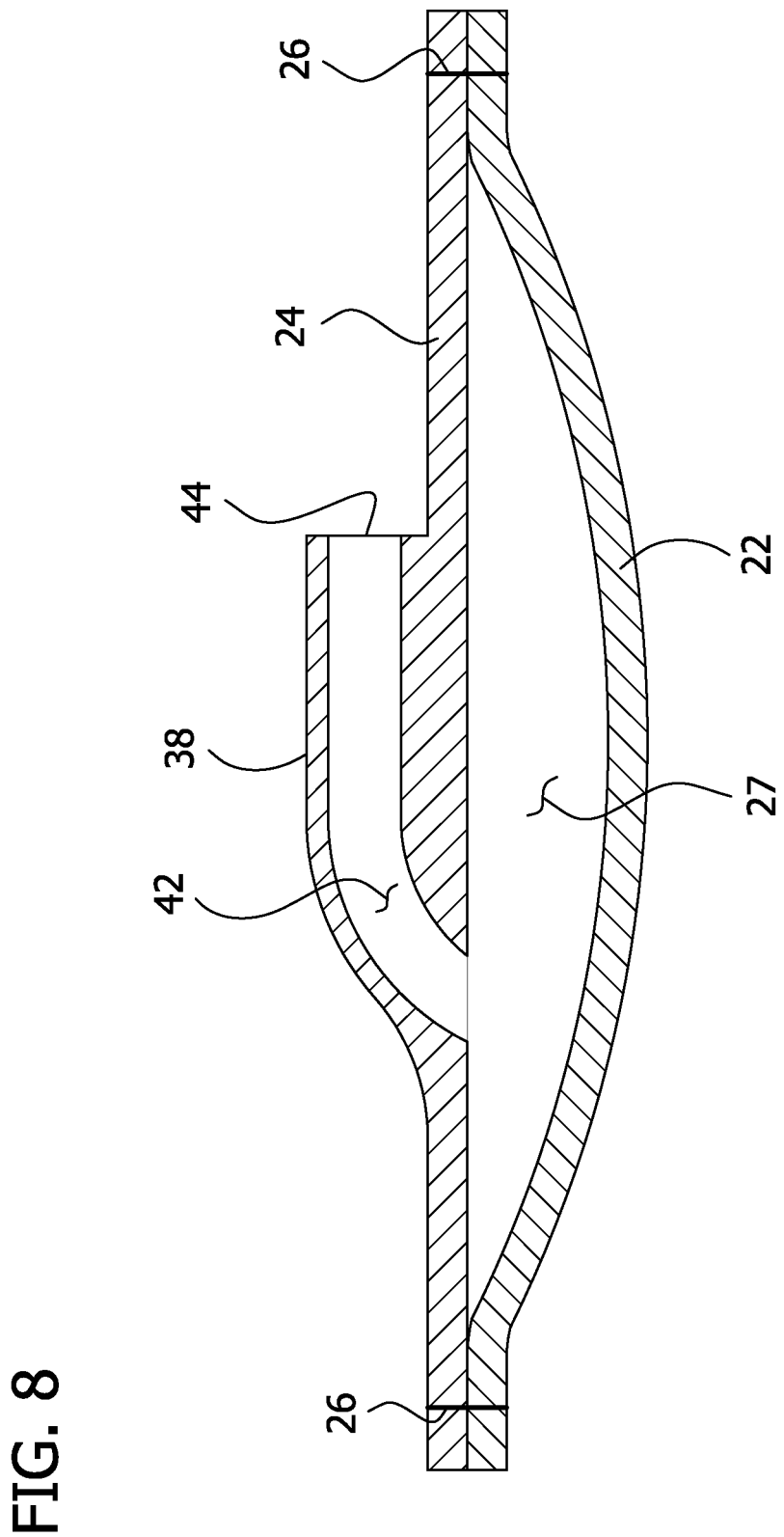
FIG. 8 is a fragmentary section taken along line 8-8 in FIG. 4.
Figure 9:
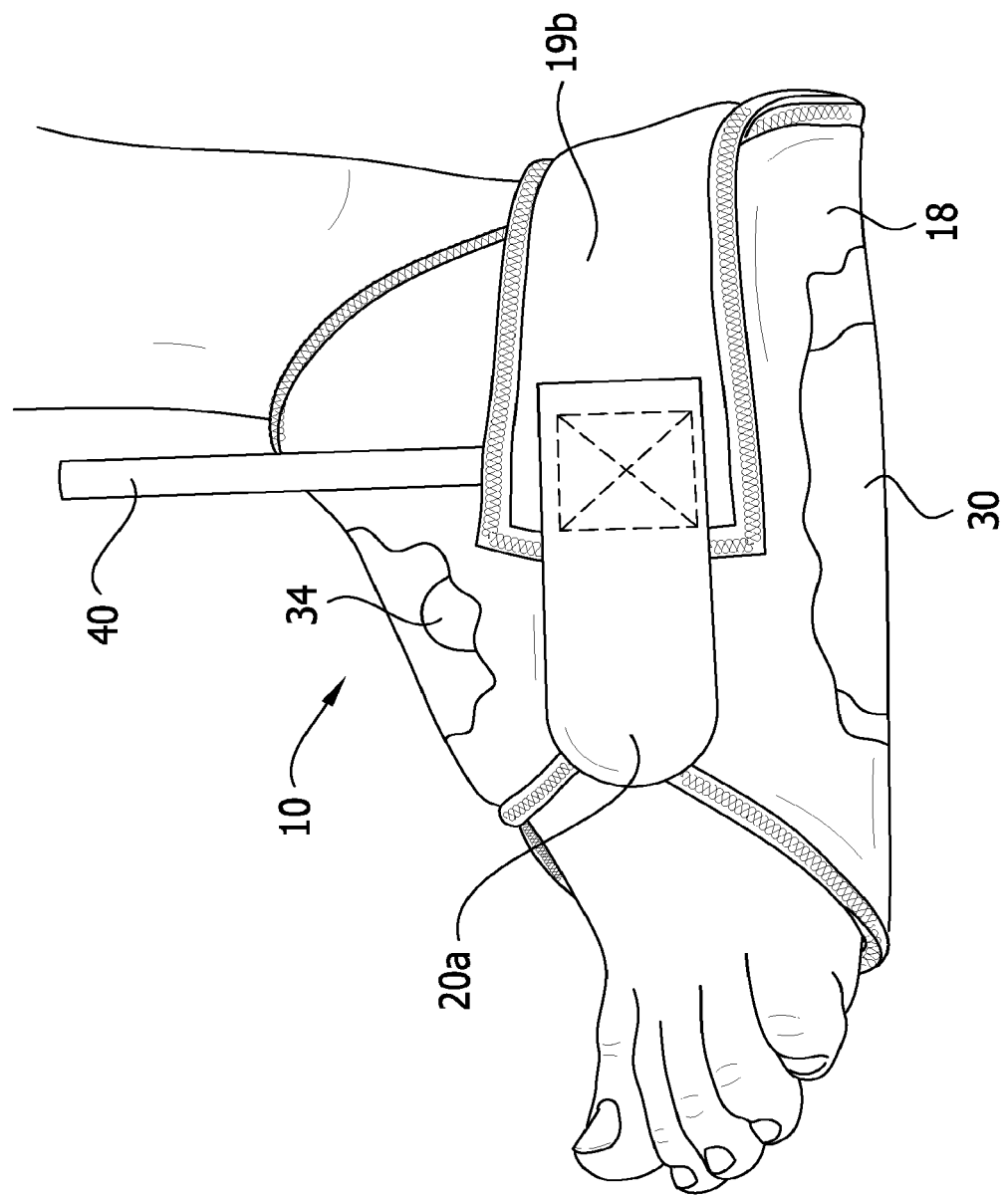
FIG. 9 is a perspective of the compression foot cuff wrapped around a foot of a wearer.

Referring to FIGS. 1B and 2-8, the bladder 14 includes inner and outer bladder layers 22, 24, respectively, of air impermeable material (e.g., PVC, rubber, etc.) joined together in a suitable manner along a line 26 generally adjacent to their peripheries to define a single inflatable chamber 27 (FIGS. 6 and 8). The inner and outer bladder layers 22, 24 may be joined to one another in a suitable manner such as by radio frequency (RF) welding. Other ways of joining the inner and outer bladder layers 22, 24 include sewing, adhesive, heat sealing, etc. The inner and outer bladder layers 22, 24 are secured together so that an inner face of the outer layer faces an outer face of the inner layer, and an outer face of the outer layer faces away from an inner face of the inner layer. The inflatable chamber 27 of the bladder 14 is adapted for receiving and retaining a pressurized fluid (e.g. air) for exerting compressive pressure to the foot during successive pressure application cycles. Moreover, the inner layer has a thickness and material properties to allow it to be easily reformed by compressed air in the inflatable chamber 27. It is understood that the bladder 14 can include more than one inflatable chamber 27 within the scope of the present invention. The bladder 14 includes a foot-underlying portion, generally indicated at 30, that is sized and shaped to underlie the wearer's foot. The thickness and rigidity of the foot-underlying portion 30 are selected so that expansion of the inflatable chamber 27 in the area of the foot-underlying portion is concentrated in a direction away from the foot underlying portion and toward the foot for increasing foot compression in this area. Extending laterally outward from the foot-underlying portion 30 of the bladder 14 is a wing portion, generally indicated at 34, that is sized and shaped to be wrapped partially around the foot to a superior portion of the wearer's foot. The material of the wing portion 34 is preferably of a low enough density to be folded over onto the top of the foot (for example and without limitation, a medium vinyl composite having a durometer of 30-40 Shore A). While bendable, the wing portion 34 provides sufficient rigidity to resist flexing out of plane under pressure during inflation of the inflatable chamber 27. It is understood that the wing portion 34 may have other shapes and sizes. It is also understood that the bladder 14 may not include the wing portion 34 within the scope of the present invention.

Referring to FIG. 6, the outer bladder layer 24 has a thickness T1 at the foot-underlying portion 30 that is greater than a generally uniform thickness T2 of the inner bladder layer 22 at the foot-underlying portion. In general, because the outer bladder layer 24 at the foot-underlying portion 30 is thicker than the inner bladder layer 22 at the foot-underlying portion, the outer bladder layer is more rigid than the inner bladder layer at the foot-underlying portion of the bladder. It is believed that by making the outer bladder layer 24 more rigid than the inner layer 22 at the foot-underlying portion 30, the outer bladder layer provides a counterforce that directs expansion of the inflatable chamber 27 toward the inner layer, the inner liner 16 and the user's foot. In this way, the inner bladder layer 22 expands inward, toward the user's foot more than the outer bladder layer 24 expands outward, away from the user's foot to direct compressive force toward the user's foot. Moreover, the thicker foot-underlying portion 30 can provide a surface on which the patient could walk so that it would be unnecessary to remove the cuff 10. For example and without being limiting, the thickness T1 of the outer bladder layer 24 at the foot-underlying portion 30 may be at least about three times as great as the thickness T2 of the inner bladder layer 22 at the foot-underlying portion 30, and more preferably, the thickness T1 is at least about ten times greater than the thickness T2, and more preferably, the thickness T1 is at least about twenty five times greater than the thickness T2. In one example and without being limiting, the thickness T1 of the outer bladder layer 24 at the foot-underlying portion 30 may measure between about 0.100 and about 0.300 inches; and the thickness of T2 the inner bladder layer 22 at the foot underlying portion 30 may measure between about 0.006 and about 0.030 inches, more preferably between about 0.006 and about 0.012 inches. The inner and outer bladder layers 22, 24 at the foot-underlying portion 30 of the bladder 14 may have other dimensions and relative sizes without departing from the scope of the present invention.

Referring to FIGS. 1B and 2-8, to further rigidify the underlying portion 30 of the outer layer, a stiffening groove 37a in the outer face of the outer bladder layer 24 and a corresponding stiffening rib 37b on the inner face of the outer bladder layer extend generally adjacent to the perimeter of the underlying portion 30 of the outer layer. The stiffening rib 37b inhibits bending of the underlying portion 30 out of its plane. This allows thickness T1 of the outer bladder layer 24 to be smaller than would be required without the rib.

Referring to FIG. 6, in the illustrated embodiment the thickness T1 of the outer bladder layer 24 at the foot-underlying portion 30 is also greater than a thickness T3 of the outer bladder layer at the wing portion 34 of the bladder 14. As stated above, the greater thickness T1 of the outer bladder layer 24 and the stiffening rib 37b at the foot-underlying portion 30 provide rigidity to the outer bladder layer so that it acts as a counterforce. In one embodiment, the thickness T3 of the outer bladder layer 24 at the wing portion 34 of the bladder 14 allows the wing portion to be generally flexible and pliable so that in use, the wing portion 34 can be folded along a side of the wearer's foot to a top of the foot. Accordingly, in one embodiment the thickness T3 of the outer bladder layer 24 at the wing portion 34 of the bladder 14 is such that the wing portion of the bladder can be wrapped around the foot. For example and without being limiting, the thickness T3 of the outer bladder layer 24 at the wing portion 34 may be at least about 1.5 times less than the thickness T1 of the outer bladder layer at the foot-underlying portion 30. In other words, the thickness T1 of the outer bladder layer 24 at the foot-underlying portion 30 may be at least about two times greater than the thickness T3 of outer bladder layer at the wing portion 34. More preferably, in one example, the thickness T3 of the outer bladder layer 24 at the wing portion 34 may be at least about between 5-15 times less than the thickness T1 of outer bladder layer at the foot-underlying portion 30. In one example given without being limiting, the thickness T3 of the outer bladder layer 24 at the wing portion 34 may measure between about 0.020 and about 0.060 inches. The outer bladder layer 24 at the wing portion 34 and the foot-underlying portion 30 of the bladder 14 may have other dimensions and relative sizes without departing from the scope of the present invention.

A fluid inlet port 38 on the outer face of the outer bladder layer 24 fluidly connects tubing 40 (FIGS. 1A and 1B) from an air compressor controller (not shown) to the inflatable chamber 27. The fluid inlet port 38 is positioned generally adjacent to a juncture of the foot-underlying portion 30 and the wing portion 34. When the cuff 10 is assembled, the fluid inlet port 38 extends through a cut-out 20 in the outer cover 18. An internal conduit 42 (FIG. 8) extends from a connecting opening 44 in the fluid inlet port 38 through the inner face of the outer bladder layer 24. The connecting opening 44 is sized and shaped to receive the tubing 40 and to secure the tubing to the fluid inlet port 38. Other ways of connecting tubing 40 to the fluid inlet port 38 are within the scope of the invention. The fluid inlet port 38 has a generally low-profile height projecting outward from the outer face of the outer bladder layer 24 so that the fluid inlet port has a cross-sectional shape that is generally oblong. It is understood that the fluid inlet port 38 may be of other shapes and configurations. For example, the fluid inlet port 38 may comprise a plastic component that is secured, such as by heat welding or other means, to the bladder 14. It is understood that other ways of introducing air or fluid into the inflatable chamber 27 are within the scope of the invention, and the tubing 40 may be fluidly connected to the inflatable chamber in other ways without departing from the scope of the invention.

Referring to FIGS. 1A and 7, in the illustrated embodiment the bladder 14 is generally fixedly secured to the inner liner 16 and the outer cover 18 using securement openings 46 extending through the foot-underlying portion 30 of the inflatable member generally adjacent to the perimeter of the foot-underlying portion. In the illustrated embodiment, the securement openings 46 are located between the perimeter edge of the foot-underlying portion 30 and the line 26 where the outer bladder layer 24 and the inner bladder layer 22 are secured to one another. The inner liner 16 and the outer cover 18 are secured to one another through these securement openings 46 to thereby secure the bladder 14 in fixed position inside the envelope 12. The inner liner 16 and the outer cover 18 may be secured to one another at securement points 48 by heat welding, adhesive bonding, mechanical fasteners or in other ways. In one example, where the outer cover 18 is of a relatively thick foam material, the inner liner 16 may be inserted through the securement openings 46 to the outer cover to secure the inner liner to the outer cover. Other ways of securing the bladder 14 to the envelope 12 to fix the relative position of the bladder with respect to the inner liner 16 and/or the outer cover 18 is within the scope of the invention. Alternatively, the bladder 14 may "float" inside the envelope 12 and not be generally fixed in a relative position with respect to the inner liner 16 and/or the outer cover 18.

In one embodiment and without being limiting, the outer bladder layer 24 may be molded, such as by injection molding, as a one-piece, integral unit.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An inflatable bladder for use in a compression foot cuff configured to be secured to a foot of a wearer, the inflatable bladder comprising:
   a fluid-impermeable inner bladder layer for being positioned adjacent to a foot of a wearer;
   a fluid-impermeable, integrally formed outer bladder layer secured in opposing relation to the inner bladder layer to define an inflatable chamber;
   wherein the inner and outer bladder layers define a foot-underlying portion of the bladder that underlies the wearer's foot when the compression foot cuff is secured to the foot of the wearer, and a wing portion extending laterally outwardly from the foot-underlying portion;
   wherein a thickness of the outer bladder layer at the foot-underlying portion is greater than a thickness of the inner bladder layer to provide rigidity to the outer bladder layer so that the inflatable chamber expands more toward the wearer's foot than away from wearer's foot when the foot cuff is secured to the wearer's foot, and the thickness of the outer bladder layer at the foot-underlying portion is greater than a thickness of the outer bladder layer at the wing portion so that the wing portion of the inflatable bladder is more flexible than the foot-underlying portion of the outer bladder layer to wrap around a superior portion of the wearer's foot, wherein the outer bladder layer has a rib formed on an inner surface of the outer bladder layer to resist bending of the outer bladder layer and wherein the rib forms a groove in an outer surface of the outer bladder layer;
   wherein the inner bladder layer and outer bladder layer are secured to each other along a line extending generally adjacent to perimeter of the inflatable bladder, the groove and rib being formed on the outer bladder layer separately from the line connecting the inner bladder layer to the outer bladder layer, the rib and groove extending only partially along the perimeter of the inflatable bladder such that the rib and groove extend a lesser distance along the perimeter than the line and extend only along the foot-underlying portion of the inflatable bladder.

2. An inflatable bladder as set forth in claim 1 wherein the thickness of the outer bladder layer at the foot-underlying portion is at least three times greater than the thickness of the inner bladder layer.

3. An inflatable bladder as set forth in claim 2 wherein the thickness of the outer bladder layer at the foot-underlying portion is at least about ten times greater than the thickness of the inner bladder layer.

4. An inflatable bladder as set forth in claim 1 wherein the thickness of the outer bladder layer at the foot-underlying portion is at least about 1.5 times greater than the thickness of the outer bladder layer at the wing portion.

5. An inflatable bladder as set forth in claim 4 wherein the thickness of the outer bladder layer at the foot-underlying portion is at least about five times greater than thickness of the outer bladder layer at the wing portion.

6. An inflatable bladder as set forth in claim 1 further comprising a fluid inlet port extending outward from the outer bladder layer for connection to a source of pressurized fluid, the inlet port defining a conduit in fluid communication with the inflatable chamber for delivering pressurized fluid to the inflatable chamber.

7. An inflatable bladder as set forth in claim 6 wherein the outer bladder layer and the inlet port are molded as a one-piece, integral unit.

8. An inflatable bladder as set forth in claim 7 wherein the inlet port has a longitudinal axis and defines a connecting opening on an exterior of the inflatable bladder, the longitudinal axis extending through the connecting opening and generally parallel to the outer bladder layer, the connecting opening having an oblong cross-sectional shape taken transverse to the longitudinal axis so that the inlet port has a low profile with respect to the outer bladder layer.

9. An inflatable bladder as set forth in claim 8 wherein the outer bladder layer and the inner bladder layer define a wing portion of the inflatable bladder extending laterally outward from the foot-underlying portion and wrapping around a superior portion of the wearer's foot when the compression foot cuff is secured to the foot of the wearer, wherein the thickness of the outer bladder layer at the foot-underlying portion is greater than the thickness of the outer bladder layer at the wing portion.

10. An inflatable bladder as set forth in claim 1 further comprising a securement opening extending through the inner and outer bladder layers adjacent to a perimeter edge of the foot-underlying portion of the bladder.

11. An inflatable bladder as set forth in claim 10 in combination with an envelope including an outer cover and an inner liner, the inflatable bladder being disposed between the outer cover and inner liner in the envelope, wherein at least one of the outer cover and the inner liner extends into the securement opening and is secured to the other of the outer cover and inner liner to fix a position of the inflatable bladder with respect to the envelope.

12. An inflatable bladder as set forth in claim 11 wherein the securement opening comprises a plurality of securement openings.

* * * * *